United States Patent
Yugawa et al.

(12)

(10) Patent No.: US 6,271,381 B1
(45) Date of Patent: Aug. 7, 2001

(54) COCAINE DERIVATIVE, PROTEIN CONJUGATE THEREOF, MONOCLONAL ANTIBODY PRODUCING CELL LINE, METHOD FOR PREPARING THE CELL LINE AND MONOCLONAL ANTIBODY

(75) Inventors: Keiko Yugawa, Kadoma; Nobuyuki Sigetoh, Osaka; Jinsei Miyazaki, Higashiosaka; Tadayasu Mitsumata, Hirakata, all of (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/706,774

(22) Filed: Nov. 7, 2000

Related U.S. Application Data

(62) Division of application No. 08/982,963, filed on Dec. 2, 1997, now Pat. No. 6,174,723, which is a continuation of application No. 08/409,950, filed on Mar. 23, 1995, now abandoned, which is a continuation of application No. 08/091,054, filed on Jul. 14, 1993, now abandoned.

(30) Foreign Application Priority Data

Mar. 4, 1993 (JP) .................................. 5-043502
Mar. 15, 1993 (JP) ................................. 5-053380

(51) Int. Cl.$^7$ ..................... C07D 401/00; C07D 451/02; A61K 39/385

(52) U.S. Cl. .................. 546/125; 546/129; 546/130; 424/193.1; 424/194.1

(58) Field of Search .................. 546/125, 129, 546/130; 424/193.1, 194.1

(56) References Cited

U.S. PATENT DOCUMENTS 5,233,042   8/1993   Buechler ......................... 546/129
5,808,074   9/1998   Gowda et al. ................... 546/130

OTHER PUBLICATIONS

American Type Culture Collection (ATTC), Catalogue of Cell Lines and Hybridomas, 7th Edition. Editors: Hay et al. ATTC: Maryland, USA, (1992).
Collison et al., J. Forensic Science, 43(2): 390–394, Santa Ana, California (1998) (Abstract).
Harlow, E. and Lane, D. Antibodies: A Laboratory Manual. Cold Spring Harbor Laboratory: New York, USA (1988).
O'Connell et al. J. Immunological Meth. vol. 225, No. 1–2, pp. 157–169. Abstract only, AN 1999291914, MEDLINE, (5/1999).

*Primary Examiner*—Jyothsna Venkat
*Assistant Examiner*—Barba M. Koroma
(74) *Attorney, Agent, or Firm*—Morrison & Foerster LLP

(57) ABSTRACT

A method for preparing a cocaine-protein conjugate easily by using a cocaine derivative having a methoxy carbonyl group and benzoyl group. This conjugate is useful for the detection of cocaine or cocaine derivatives.

4 Claims, 2 Drawing Sheets

COCAINE DERIVATIVE, PROTEIN CONJUGATE THEREOF, MONOCLONAL ANTIBODY PRODUCING CELL LINE, METHOD FOR PREPARING THE CELL LINE AND MONOCLONAL ANTIBODY

This application is a division of U.S. application Ser. No. 08/982,963, filed Dec. 2, 1997, now U.S. Pat. No. 6,174,723, which is a continuation of application Ser. No. 08/409,950, filed Mar. 23, 1995, now abandoned, which is a continuation of application Ser. No. 08/091,054, filed Jul. 14, 1993, now abandoned.

FIELD OF THE INVENTION

The present invention relates to a cocaine-protein conjugate for use as an antigen to produce an anti-cocaine antibody, a cocaine derivative as a starting material for the conjugate, a novel monoclonal antibody producing cell line obtained from the antigen and a monoclonal antibody produced by the cell line. The monoclonal antibody is useful in immunochemically detecting cocaine or its derivative out of blood or air with high sensitivity.

BACKGROUND OF THE INVENTION

J. Pharmacol. Exp. Ther., vol.199, p171 (1976) proposes a synthesis of an anti-cocaine antibody for use in an immunoassay for cocaine, and an antigen necessary in preparing the antibody. The antibody reported is, however, a polyclonal antibody which can be obtained from refined blood of a goat or rabbit immunized using an antigen of ecgonine of Formula (1).

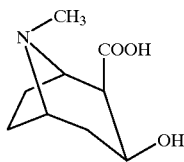

Formula (1)

To obtain an anti-cocaine antibody highly specific for cocaine, a cocaine-protein conjugate must be formed by using a derivative keeping the cocaine framework as precise as possible. Unfortunately, ecgonine lacks a methoxycarbonyl group and benzoyl group each characteristic of the cocaine molecule.

The polyclonal antibodies of the prior art can simply be prepared; on the other hand, it is less reproducible because the properties of the prodluct depend on individual experimental animals. Thus, it is quite difficult to provide antibodies of the same quality.

Polyclonal antibodies are a mixture of a diversity of antibodies having respective affinities. All the affinities they have prevent the use of a polyclonal antibody in a sensitive detection system because of their low affinity for the molecule of interest. In accordance with the above, we tried to obtain a monoclonal antibody having high affinity for cocaine; however, we could not succeed because ecognine as an antigen is too different in structure from cocaine.

SUMMARY OF THE INVENTION

The invention aims to provide a method for easily preparing a cocaine-protein conjugate based on cocaine characterized by a methoxy carbonyl group and a benzoyl group.

The invention further aims to provide a monoclonal antibody of high affinity for cocaine or cocaine derivatives by immunizing with the cocaine-protein conjugate.

The invention further aims to provide a cell line for producing the monoclonal antibody.

To attain the above-mentioned aims, the inventors brought about an amino derivative of cocaine based on norcocaine substituted with an amino alkyl group in its secondary amino group, a pyridyl dithio derivative of an amino cocaine derivative substituted with a 3-(2-pyridyl dithio)propynoyl group in its amino group, and a cocaine-protein conjugate. Further, the inventors established a monoclonal antibody producing cell line by fusing a spleen cell derived from mouse immunized with an antigenic cocaine-protein conjugate and a cell line derived from a myeloma cell culture and cloning the fusion.

A first compound of the invention is shown in Formula (2):

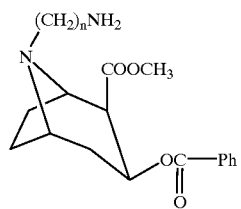

Formula (2)

wherein n is an integer of 1 or more and Ph is a benzene ring.

A first cocaine-protein conjugate is the above cocaine derivative conjugated to a protein.

A second compound of the invention is shown in Formula (3):

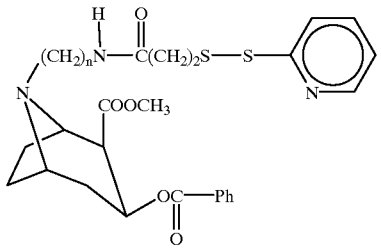

Formula (3)

wherein n is an integer of 1 or more and Ph is a benzene ring.

A second cocaine-protein conjugate is the second cocaine derivative conjugated to a protein by a disulfide bond.

The method for preparing a monoclonal antibody producing cell line comprises fusing a spleen cell derived from a mouse immunized with an antigen of the first cocaine-protein conjugate and a cell line derived from a myeloma cell line and cloning the fusion.

It is preferable in the above method that the protein is keyhole limpet hemocyanin.

It is also preferable in the above method that the cell line derived from a myeloma cell line is P3X63-Ag8.653.

It is also preferable in the above method that the mouse is derived from an A/J strain.

The cell line of the invention is preferably a monoclonal antibody producing cell line deposited in the National Institute of Bioscience and Human Technology 1-3, Higashi 1-chome, Tsukuba-shi, Ibaraki-ken 305 Japan as No.BP-4177 produced with the above method, characterized by producing an antibody capable of specifically binding to cocaine or cocaine derivatives.

The invention further aims to provide a monoclonal antibody from the above monoclonal producing cell line.

With the amino derivatives of cocaine of the invention, one can readily prepare a pyridyl dithio derivative of an amino cocaine derivative having a disulfide group capable of linking to a protein, keeping the cocaine framework as it is. By immunizing a test animaal with a cocaine-protein conjugate made from the above pyridyl dithio derivative, one can get a cell line for producing an antibody of higher affinity for cocaine because the cocaine-protein conjugate holds the cocaine framework.

After immunoreaction, antibody-producing cells are stored in the spleen. Although a spleen is unable to reproduce by itself, it can proliferate and produce a hybridoma cell line by fusing with a cell line derived from myeloma. The hybridoma cell line vigorously produces antibodies as it proliferates. By selecting a hybridoma cell which has much multiplication ability and produces an antibody having the highest affinity for a certain molecule and cloning the hybridoma, one can produce a desired monoclonal antibody. The monoclonal antibody thus obtained is a single kind of antibody, and of high-affinity. A constant quality of monoclonal antibody can permanently be provided by culturing the hybridoma.

DETAILED DESCRIPTION OF THE INVENTION

Figure 1:
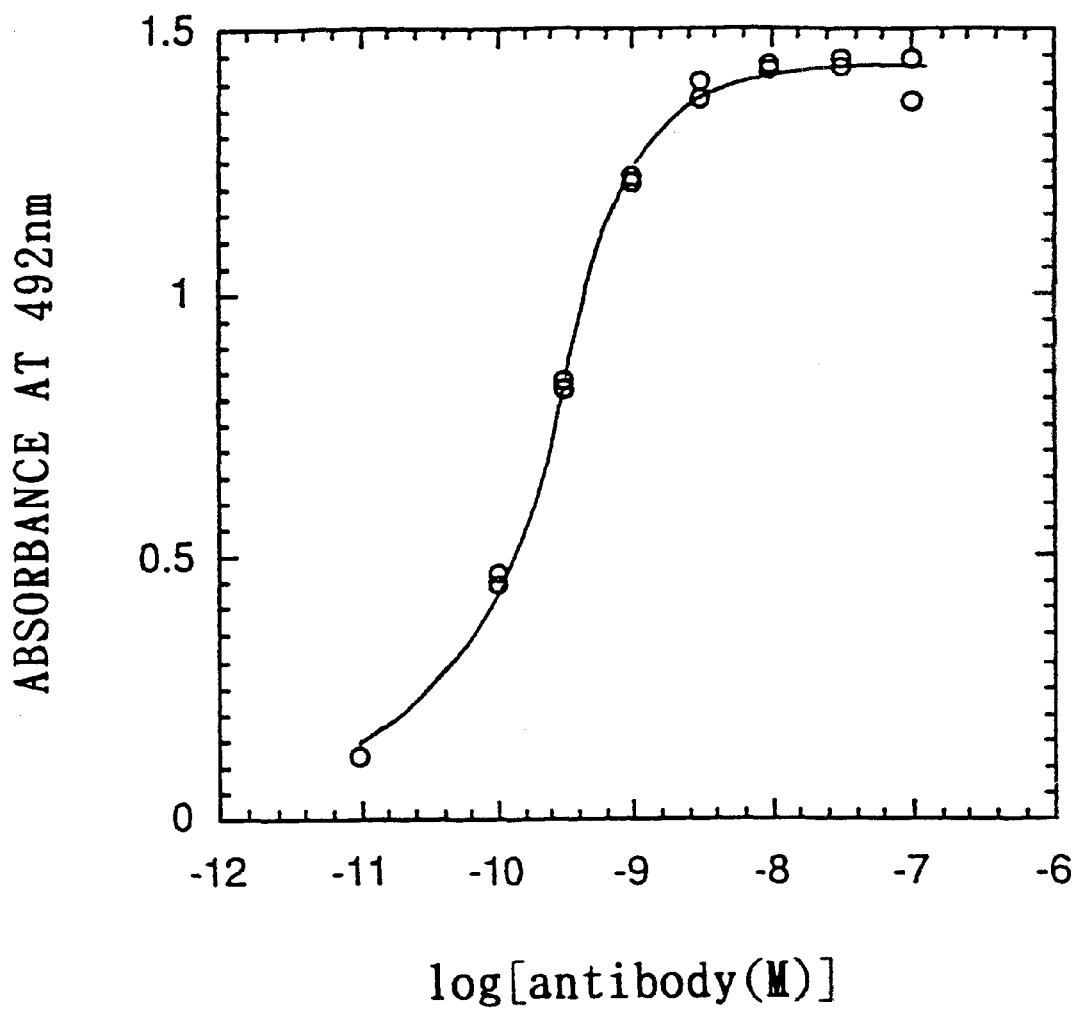
FIG. 1 is a graph showing the binding ability of monoclonal antibody for an antigen in solid phase with an ELISA assay in an embodiment of the invention.

In the preferred embodiments of the invention, an amino derivative of cocaine is obtained from norcocaine and an amino group. The amino group is, for example, $X(CH_2)_nR$ where X is a halogen, n is an integer of 1 or more, and R is succinimidyl or maleimidyl or fumarimidyl.

A pyridyl dithio derivative of cocaine is obtained by introducing a 3-(2-pyridyldithio)propynoyl group to the above amino derivative.

What protein is suitable as a carrier depends on both the test animal and the antigen. Our experiments using a variety of proteins such as chicken-gamma-globulin, bovine serum globulin, or keyhole limpet hemocyanine revealed that keyhole limpet hemocyanin (hereinafter abbreviated as KLH) was the best possible carrier protein in the practice of the invention.

To obtain a cell line producing a monoclonal antibody of high affinity, one needs to attain antisera of high antibody titer. Such an immune response depends on the kind and strain of the experimental animals. The inventors immunized different kinds of mice such as A/J, BALB/c, DBA/2, C57BL/6, C3H/He and found that an A/J mouse was the best candidate to produce an antiserum with the highest titer.

Finally, the proliferation ability of a hybridoma depends largely on the kind of cell line derived from the mouse myeloma in the cell fusion. Our experiments using a cell line derived from a diversity of mice revealed that a cell line of P3X63-Ag8.653 makes a hybridoma proliferate at the possible best speed.

The embodiments of the invention will be hereinafter be explained with reference to a cocaine derivative, a 2-pyridyl dithio derivative of cocaine, a cocaine-protein conjugate, a method for producing monoclonal antibody producing cell line, a monoclonal antibody, and finally detection of cocaine therewith.

EXAMPLE 1

A method for preparing an amino derivative of cocaine will be explained with reference to an example using an aminobutyl group. Firstly, norcocaine was prepared from cocaine. Then, the norcocaine was reacted with butyl phthalimide to form the object amino derivative.

(A) Preparation of Norcocaine

Norcocaine of Formula (4) was prepared as follows.

Cocaine (500 mg) was dissolved in a mixture (21 ml) of acetonitrile and water (1:2). Acetic acid (0.5 ml) was added to the solution to adjust its pH to approximately 5. To the solution was added dropwise 21 ml aqueous potassium permanganate ($KMnO_4$=534 mg, 3.78 mmol, 2.05 eq.) over 3 hours. The solution was stirred overnight at room temperature. After removing the resulting precipitate by filtration, potassium carbonate (1050 mg) was added to the filtrate to adjust its pH to approximately 8. The filtrate was extracted with ether three times and dried over anhydrous sodium sulfate overnight. The sodium sulfate was removed out of the extract and ether was distilled off under reduced pressure to give colorless liquid. The liquid was purified by silica-gel thin layer chromatography (hereinafter abbreviated as TLC) using as an eluent ammonia saturated chloroform to give norcocaine (269 mg) of Formula (4):

Formula (4)

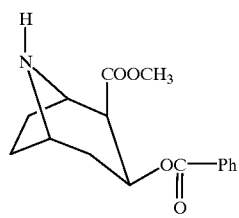

Yield: 56%

Then, norcocaine was reacted with butyl phthalimide to form an object amino derivative.

(B) Introduction of Butyl Phthalimide to Norcocaine

The butyl phthalimide derivative of norcocaine of Formula (5) was prepared as follows.

Norcocaine (268 mg, 0.93 mmol), bromo butylphthalimide (314 mg, 1.11 mmol, 1.2 eq.) and anhydrous sodium carbonate (147 mg, 1.39 mmol, 1.5 eq.) were dissolved in benzene(10 ml) and the mixture was refluxed under nitrogen atmosphere for 72 hours. After cooling to room temperature, the solution was filtered. The filtrate was extracted with 1N hydrochloric acid three times, and the aqueous layer was extracted with chloroform three times. The extract was dried over anhydrous sodium sulfate, and chloroform was distilled off under reduced pressure to give colorless crystal. The crystal was purified by TLC (eluent: ammonia saturated chloform/benzene=1/3) to give a butyl phthalimide derivative (270 mg) of Formula (5):

Formula (5)

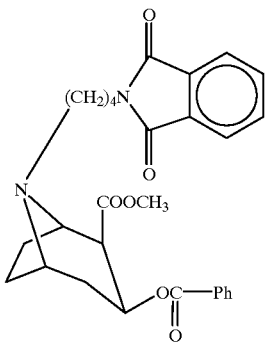

Yield: 60%

(3) Preparation of an Amino Derivative

The amino derivative of Formula (6) was prepared as follows.

Butyl phthalimide derivative of Formula (5) (100 mg, 0.20 mmol) was dissolved in 95% ethanol (3 ml), to which hydrazine hydrate (0.20 mmol) was added before a 2-hour reflux. The reaction mixture was purified by TLC (eluent: ammonia saturated chloroform/methanol=10/1) to give an amino derivative (57 mg) of Formula (6):

Formula (6)

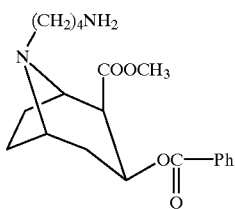

Yield: 78%

Bromo alkylphthalimide was used for preparation of the amino derivative in the above embodiment. However, other amino groups containing an amino alkyl group were also suitable.

EXAMPLE 2

The 2-pyridyl dithio derivative of cocaine of Formula (7) was prepared as follows.

The above amino derivative (84 mg, 0.23 mmol) prepared as in Example 1 was dissolved in ethanol (1 ml). To the solution was added dropwise a solution of o-succinimidyl-3-(2-pyridyl-dithio)-1-propionate (hereinafter abbreviated as SPDP (73 mg, 0.23 mmol) in ethanol (1 ml). After stirring at room temperature for 1 hour, the solution was purified by TLC (eluent:ammonia saturated chloroform) to give a 2-pyridyl dithio derivative (133 mg) of Formula (7):

Formula (7)

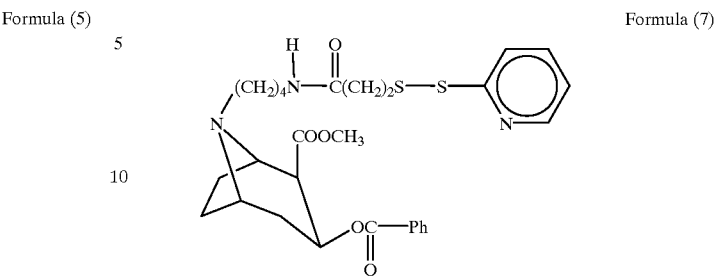

Yield: 100%

In the above embodiment, the starting material was an amino butyl derivative. Instead of that, other amino alkyl derivatives were usable as well.

In the above embodiment, SPDP was used to introduce a pyridyl dithio group to the amino cocaine derivative. Instead of SPDP, other compounds were usable as well as long as they contain a 3-(2-pyricdyl-dithio)propynoyl group.

EXAMPLE 3

A method for preparing a cocaine-protein conjugate will be explained with reference to an example using KLH. Firstly a complex of KLH and SPDP (hereinafter abbreviated as KLH-SPDP) was prepared. Then a cocaine-KLH conjugate was produced.

(A) Preparation of KLH-SPDP

KLH (200 mg) was dissolved in 30 ml phosphate buffer saline (hereinafter abbreviated as PBS). To the solution was added dropwise 0.5 ml SPDP (9.4 mg, 15 eq.) in ethanol while stirring at room temperature for 30 minutes. The resulting precipitate was removed by a 10 min centrifugation at 20000 rpm. The obtained supernatant was subjected to gel filtration chromatography using a 2×80 cm SEPHADEX® G25 column (Pharmacia Fine Chemicals) to give a solution of KLH-SPDP in PBS (40 ml). The number of SPDP binding to a KLH molecule was determined as follows.

Out of the solution of KLH-SPDP in PBS thus obtained, a volume of 1 ml was used to measure absorbance at 280 nm. The absorbance ($A_{280}$) was 3.6005. To the solution was added 50 μl of 100 mM aqueous dithiothreitol solution (hereinafter abbreviated as DTT). After 5 minutes, the solution was used to measure absorbance at 343 nm. The absorbance ($A_{343}$) was 1.576. The concentration of pyridin-2-thione was calculated as shown in Formula (8), provided that $1.12 \times 10^5$ was a 343 nm molecular absorption coefficient of the pyridin-2-thione released from the DTT reduction.

[pyridin-2-thione]=$1.576/1.12 \times 10^5 = 1.9505 \times 10^{-4}$(M)   Formula (8)

Hereinafter, a compound name in brackets means a molar concentration of the compound.

The concentration is equivalent to that of SPDP introduced to KLH.

Besides, the 2-pyridyl sulfide group in SPDP contributes largely to $A_{280}$ so that the following correction is needed to calculate the concentration of KLH. $A_{280\ KLH}$ depending on KLH is calculated as follows:

$A_{280\ KLH} = 3.6005 - (1.9505 \times 10^{-4} \times 5.1 \times 10^3) = 2.6057$, provided that $5.1 \times 10^3$ was a 280 nm molecular absorption coefficient of the 2-pyridyl-disulfide group. Consequently, the KLH concentration and the number of SPDP molecules introduced to a KLH molecule are calculated in accordance with Formula (9):

$$[KLH]=2.6057/1.12\times10^5=2.3265\times10^{-5}(M); [SPDP]/[KLH]=1.9505\times10^{-4}/2.3265\times10^{-5}=8.3 \quad \text{Formula (9)}$$

(B) Preparation of a Cocaine-KLH Conjugate

A cocaine-KLH conjugate was prepared as follows.

DTT (77.1 mg, 50 eq.) was added to 40 ml KLH-SPDP/PBS solution ($2.3265\times10^{-5}$M), followed by stirring at room temperature for 30 minutes. After removing the resulting precipitate by a 10 min centrifugalion at 20000 rpm, the obtained supernatant was subjected to gel filtration chromatography using a 2×80 cm Sephadex G25 column (Pharmacia Fine Chemicals) to give 48 ml KLH-SPDP (SH free)/PBS solution ($1.7316\times10^{-5}$M). To the given solution was added 4.63 mg ($8.312\times10^{-3}$ mmol) of the pyridyl dithio derivative of Formula (7), followed by stirring at 4° C. overnight. After removing the resulting precipitate by a 10 min centrifugation at 20000 rpm, the obtained supernatant was used to measure absorbance at 343 nm ($A_{343}$). The absorbance was 1.0352.

The obtained supernatant was subjected to gel filtration chromatography using a 2×80 cm Sephadex G25 column (Pharmacia Fine Chemicals) to give 48 ml cocaine-KLH/PBS solution.

The number of the pyridyl dithio, derivative binding to a KLH molecule was determined as follows. The fact that $A_{343}$ just after reaction was 1.0352 and that $8.08\times10^3$ was a 343 nm molecular absorption coefficient of pyridin-2-thione released induced that a concentration of pyridin-2-thione was calculated as shown in Formula (10):

$$[\text{pyridin-2-thione}]=1.0352/8.08\times10_3=1.2812\times10^{-4}(M) \quad \text{Formula (10)}$$

The concentration is equivalent to that of the pyridyl dithio derivative introduced to KLH.

Because the KLH concentration was $1.7316\times10^{-5}$ M, the number of pyridyl dithio derivative molecules introduced to a KLH molecule is calculated in accordance with Formula (11):

$$[\text{pyridyl dithio derivative}]/[KLH]=1.2812\times10^{-4}/1.7316\times10^{-5}=7.4 \quad \text{Formula (11)}$$

This indicates that in a cocainae-KLH conjugate 7.4 molecules of cocaine bind to a KLH molecule.

In the above embodiment, an antigen was prepared using KLH as a protein. In accordance with the present invention, an immunogen for the preparation of a monoclonal antibody producing cell line can similarly be prepared using other carrier proteins such as bovine serum albumin or chicken-gamma-globulin instead of KLH.

EXAMPLE 4

Production of a monoclonal antibody producing cell line and a monoclonal antibody.

A method for producing a monoclonal antibody producing cell line and a monoclonal antibody will be explained one by one with reference to the following embodiments.

(A) Preparation of Adjuvant Emulsion

The cocaine-KLH conjugate (hereinafter abbreviated as CC-KLH), which was obtained by a series of processes in Examples 1, 2 and 3, was diluted with PBS to adjust its concentration to 1 mg/ml. Out of an adjuvant (Freund's complete adjuvant containing heat killed and dried Mycobacterium tuberculosis, Wako Pure Chemical Industries, Ltd., H37Rv), 6 ml volume was taken while stirring vigorously. To the adjuvant was added gradually 6 ml CC-KLH solution in three times while stirring with a homogenizer (10000 rmp) to emulsify until a few drops of water did not spread on the solution any more.

(B) Immunization of Mouse

Every 100 μl of the prepared adjuvant emulsion containing CC-KLH was injected intraperitoneally to each of ten 8-year-old mice (A/J).

(C) Recognition of Antibody Production

After 70 days since the immunogenic injection, 50 to 100 μl blood out of immunized mouse from ophthalmic veins was sampled into a centrifugal tube. Serum was isolated by centrifugation, and ELISA screening revealed that every mouse produced an anti-cocaine antibody.

(D) Booster Shot to Mouse

A booster shot (supplementary weak immunogenic injection) was given to two mice to enlarge their spleen.

The two mice showed higher reactivity than any other mice in the above screening. Adjuvant-free CC-KLH solution (1 mg/ml) diluted with PBS was used as an immunogen. This immunogen (100 μl) was injected intraperitoneally to the two mice after 71 days since the immunogenic injection.

(E) Cell Fusion

A spleen cell was taken out of the mice after 3 days since the booster shot. The cell was fused with a cell line (P3X63-Ag8.653) derived from a mouse myeloma by a conventional way using polyethylene glycol of an average molecular weight 1500. A spleen cell from the same mice as the feeder (growth factor producing cell) was cultured on two 96-well plates each containing HAT medium with 15 wt % fetal calf serum (hereinafter abbreviated as FCS). A week later, HAT medium was replaced with HT medium containing 15 wt % FCS.

(F) Cloning

ELISA screening was carried out to select 12 wells showing the highest antibody titer out of all the wells. All the liquid in the selected 12 wells were collected and diluted with a medium containing 15 wt % FCS to a concentration of a single cell per well (limiting dilution). It was equally divided to 12 sheets of 96-well microplates. To accelerate initial proliferation, thymus gland cell of a 5 week-year-old mouse (Balb/c) was used as a feeder cell. After every culture using different size of plates, 24-well and 6-well plates, ELISA screening for serum was repeated to pick up a cell line which could exhibit higher antibody titer for cocaine and multiply well. The final concentration of the cell culture was $5\times10^5$ cells/ml.

(G) After Removing the supernatant, the finally selected cell line in a concentration of $5\times10^6$ cells/ml was floated in a solution of FCS and dimethylsulfoxide (9:1) and frozen at −80° C. The frozen cell line was then kept at −135° C. for future use.

(H) Monoclonal antibodies were purified by affinity chromatography using a protein A binding gel (protein A SEPHAROSE®, CL-4B, Pharmacia) from the supernatant of cell culture. SDS polyacrylamide gel electrophoresis revealed that the purified monoclonal antibody was IgG consisting of the Heavy chain (approximately 50000 molecular weight) and the Light chain (approximately 20000 molecular weight) compared with protein standards.

In the above embodiment, KLH was used as a protein to bind with cocaine. In accordance with the present invention, a monoclonal antibody producing cell line can similarly be produced using other carrier proteins such as bovine serum albumin or chicken-gamma-globulin instead of KLH.

EXAMPLE 5

Detection by ELISA

Evaluation of the antiserum obtained by the processes as in Example 4 and culture supernatant, and detection of cocaine or cocaine derivatives were performed by an ELISA assay using the monoclonal antibody.

(A) Antigen Coating

An antigenic solution of BSA in a concentration of 0.1 mg/ml was prepared by diluting with PBS containing 0.4 wt % sodium azide, a conjugate prepared in the way similar to CC-KLH preparation where a cocaine molecule binds to a BSA molecule in a ratio of 1:1. This solution will be abbreviated as BSA.PBS.Az. The antigenic solution was equally placed into a 96well vinyl-chloride microplate (Coster) in a concentration of 100 μl/well. The microplate was allowed to stand at 20° C. overnight.

After antigenic solution was removed with an aspirator, the plate was washed three times with PBS, which was then removed completely with an aspirator.

(B) Blocking

BSA. PBS.Az solution was placed into the plate in a concentration of 250 μl/well. The microplate was allowed to stand at room temperature for 30 minutes before removing BSA.PBS.Az with an aspirator. Unless the plate was used that day, the plate was preserved on a wet filter paper in an airtight container at 4° C. for future use.

(C) Reaction of the Antibody

Antibody solutions such as antiserum, culture supernatant, or purifed antibody, each of which was diluted in different concentrations with a BSA.PBS.Az solution, were placed into the above plate in a concentration of 100 μl/well. Inhibition solution (50 μl/well), i.e., cocaine, norcocaine, ecgonine, methylecgonine, and benzoylecgonine solutions, was placed into the plate, followed by addition of the antigenic solution (50 μl/well) while shaking. The plate was kept at room temperature for 3 hours. Then, the antigenic solution was removed with an aspirator and the plate was washed three times with PBS, which was then removed completely with an aspirator.

(D) Secondary Antibody Reaction

A secondary antibody solution of 0.2 μg/ml peroxidase-labelled goat antimouse IgG (KLP, Cat.141806 lot. HL10-5) in PBS containing 1 wt % BSA was placed into the plate in a ratio of 50 μl/well. The plate was allowed to stand at room temperature for 30 minutes. Then, the secondary antigenic solution was removed with an aspirator and the plate was washed three times with PBS, which was then removed completely with an aspirator.

(E) Termination of Substrate Reaction o-Phenylene diamine for biochemical use (40 mg) was dissolved in 10 ml citric acid-phosphate buffer (pH=5). To the solution was added a substrate solution of 30 wt % aqueous hydrogen peroxide (4 μl) to a concentration of 100 μl/well, and the mixture was allowed to stand at room temperature for 10 minutes. Then, the reaction was terminated with 4N sulfuric acid in a concentration of 25 μl/well.

(F) Measurement

The absorbance at more than 492 nm was measured using a TOYOSODA MICRO PLATE READER. A reference value was usually given in a first row of wells each containing purified water. A control value of absorbance for the wells going through no (c) process was used appropriately.

FIG. 1 shows the binding ability between each concentration of a monoclonal antibody solution and CC-BSA as a solid phase antigen coating the plate. Vertical and horizontal lines in FIG. 1 show the absorbance and the logarithm of the antibody concentration mole/l (hereinafter referred to as M), respectively.

As FIG. 1 indicates, the binding is saturated in a concentration of more than $10^{-9}$M; that is, inhibition value at $10^{-9}$M cocaine is zero or more.

Figure 2:
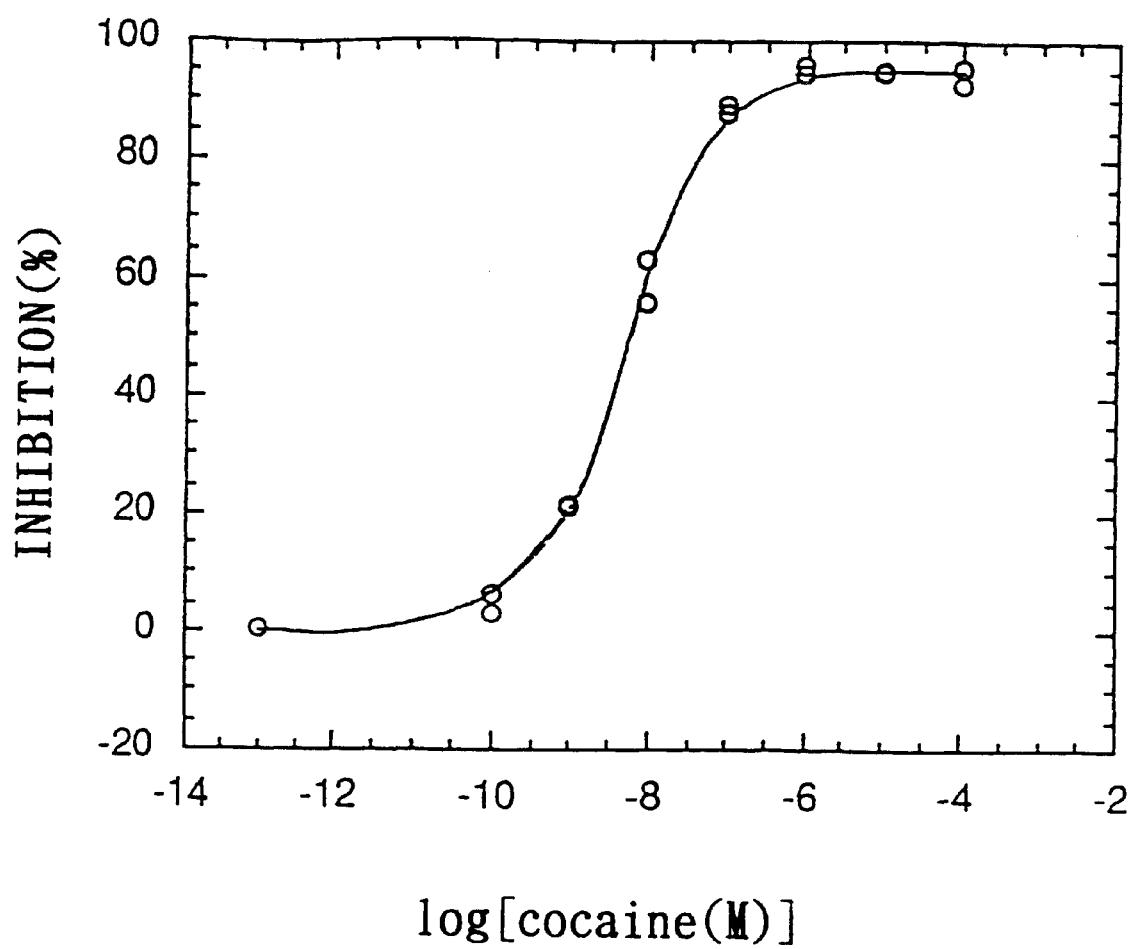
FIG. 2 is a graph showing results of detecting cocaine with the ELISA method using a monoclonal antibody of an example of the invention.

Next, the detection for each concentration of cocaine using $10^{-9}$M antibody is shown in FIG. 2. Vertical and horizontal lines in FIG. 2 show the inhibition (%) and the logarithm of the cocaine concentration (M), respectively.

Inhibition (%) was calculated as follows:

Inhibition (%)=(1−$OD_x$/$OD_{max}$)×100

$OD_x$: Absorbance at xM cocaine $OD_{max}$: Absorbance at 0M cocaine

With this detection method, an increase in cocaine concentration results in a decrease in absorbance. Thus, inhibition as shown above will rise together with cocaine concentration.

As shown in FIG. 2, $10^{-9.0}$M cocaine was detected under these conditions.

Incidentally, the monoclonal antibody seems to have fair affinity for structually related substances of the corresponding immunogen. Cocaine derivatives will be detected with a monoclonal antibody produced by the immunomethodology using CC-KLH though that detectability was rather reduced.

Here are presented relative sensitivities for cocaine and its derivatives in the same way as referred to above.

| | |
|---|---|
| norcocaine | 10 |
| ecgonine | 13 |
| methylecgonine | 20 |
| benzoylecgonine | 30 |

The term relative sensitivity means the lowest detectable concentration ratio of every substance to that of cocaine. A higher figure means lower detectability.

As explained above, the invention provides a cocaine-protein conjugate having methoxy carbonyl and benzoyl groups both characteristic of cocaine from an amino derivative of norcocaine substituted with an amino alkyl group in its secondary amino group, and a pyridyl dithio derivative of the above amino derivative substituted with 2-pyridyl dithio propynoyl group in its amino group.

Further, the invention provides a monoclonal antibody with high affinity for cocaine or cocaine derivatives and a monoclonal antibody producing cell line.

What is claimed is:

1. An amino derivative of cocaine of Formula I

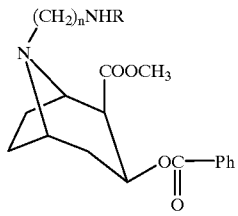

(Formula I)

where R is either H or R'; and where R' is:

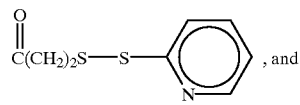

(Formula II)

wherein n=1 to 4 and Ph is a benzene ring.

2. The cocaine derivative of claim 1, conjugated to a protein.

3. The cocaine derivative of claim 1, conjugated to a protein by a disulfide bond.

4. The cocaine derivative of claim 2, wherein the protein is keyhole limpet hemocyanin.

* * * * *

UNITED STATES PATENT AND TRADEMARK OFFICE
CERTIFICATE OF CORRECTION

PATENT NO. : 6,271,381 B1  
DATED : August 7, 2001  
INVENTOR(S) : Keiko Yugawa et al.

Page 1 of 1

It is certified that error appears in the above-identified patent and that said Letters Patent is hereby corrected as shown below:

Column 3,
Line 9, change "animaal" to -- animal --;

Column 7,
Line 43, change "cocainae-KLH" to -- cocaine-KLH --; and
Line 65, change "rmp" to -- rpm --; and Column 9,
Line 20, change "purifed" to -- purified --.

Signed and Sealed this

Fifth Day of March, 2002

Attest:

JAMES E. ROGAN
*Attesting Officer*  *Director of the United States Patent and Trademark Office*